United States Patent [19]

Souren-Franssen et al.

[11] Patent Number: 5,782,777
[45] Date of Patent: Jul. 21, 1998

[54] STAGING OF DEMENTIA SEVERITY BY JOINT FUNCTION EXAMINATION

[76] Inventors: Liduin E. M. Souren-Franssen; Emil H. Franssen, both of 595 Main St., #1102, New York, N.Y. 10044; Barry Reisberg, 20 Waterside Pl., #7K, New York, N.Y. 10010

[21] Appl. No.: 662,062

[22] Filed: Jun. 12, 1996

Related U.S. Application Data

[63] Continuation-in-part of Ser. No. 390,359, Feb. 17, 1995, abandoned.

[51] Int. Cl.[6] ............................................. A61B 5/103
[52] U.S. Cl. ............................................. 600/587
[58] Field of Search ............................... 128/774, 781, 128/782

[56] References Cited

U.S. PATENT DOCUMENTS

| | | | |
|---|---|---|---|
| 5,263,492 | 11/1993 | Voyce | 128/782 |
| 5,469,862 | 11/1995 | Kovacevic | 188/782 |

*Primary Examiner*—Robert A. Hafer
*Assistant Examiner*—Pamela L. Wingood
*Attorney, Agent, or Firm*—Gottlieb, Rackman & Reisman, P.C.

[57] ABSTRACT

The clinical severity of Alzheimer's Disease in the elderly may be determined by measurement of contractures which correlate with the clinical severity of the disease. A goniometer may be used to determine the existence and degree of such contractures.

6 Claims, 2 Drawing Sheets

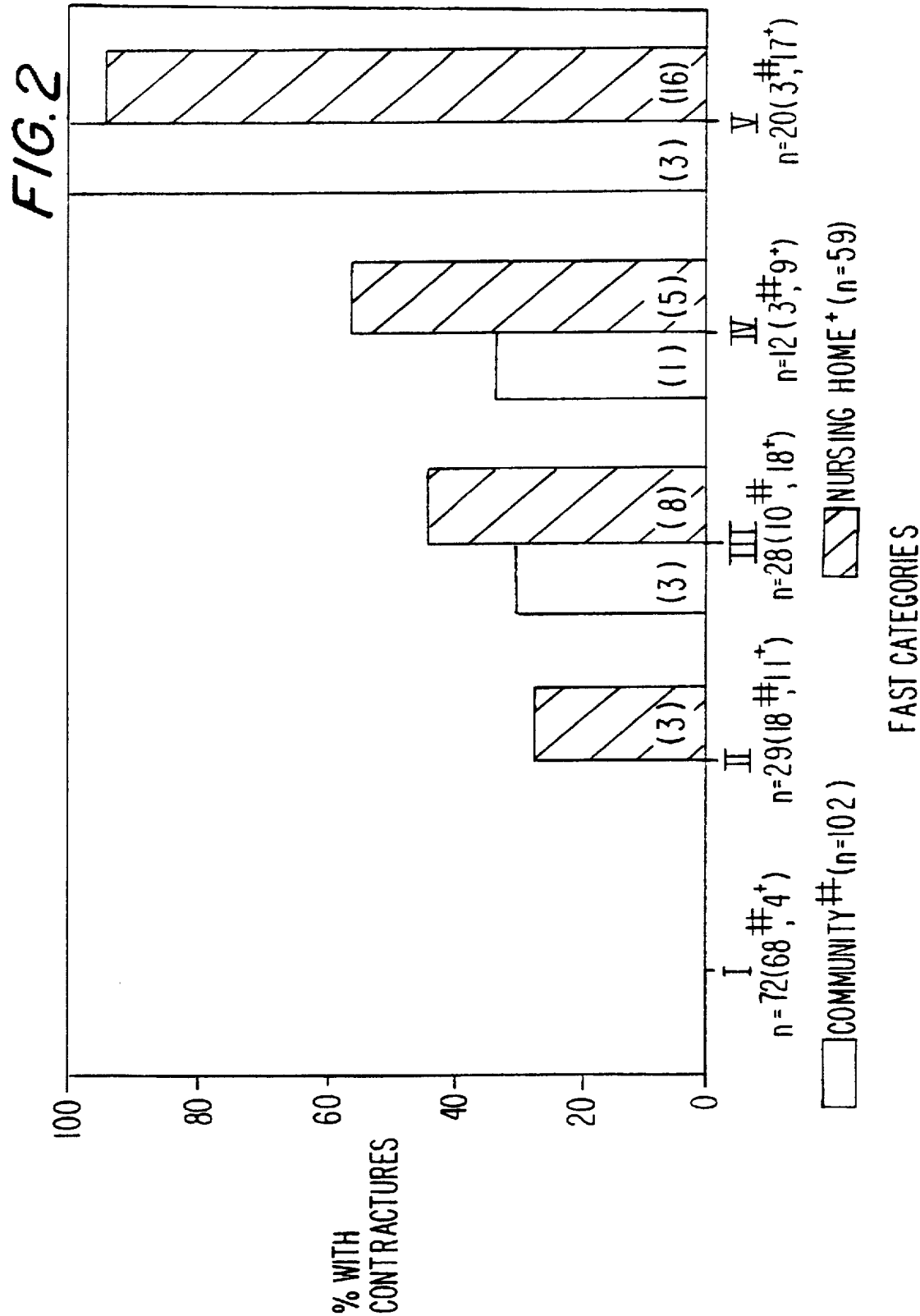

STAGING OF DEMENTIA SEVERITY BY JOINT FUNCTION EXAMINATION

This application is a continuation-in-part of application Ser. No. 08/390,359, filed Feb. 17, 1995, now abandoned.

FIELD OF THE INVENTION

This invention relates to methods of joint function examination for the staging of the severity of dementia. It operates by detecting the presence of joint contractures in patients and by determining the association between contractures and cognitive and functional decline in Alzheimer disease.

The invention has important application to methods of joint function examination for the determination of quality of life and quality of care for patients with dementia, by detecting the presence of contractures.

BACKGROUND OF THE INVENTION

Alzheimer's disease (AD) afflicts approximately 4 million persons in the United States. The late stages of AD are characterized by a progressive and devastating loss of functional capabilities. Alois Alzheimer described the terminal stage in his patient: "she was confined to bed in a fetal position (with legs drawn up), was incontinent and in spite of all the care and attention given to her she suffered from decubitus." The AD patient eventually suffers the loss of control over bladder and bowel discharge, and loses verbalization capacity and locomotor function. Ultimately, an overall dissolution of motor function, commonly accompanied by a pathological increase in muscle tone, particularly of the flexors, causes almost total immobility.

Contractures can be either a cause or a result of immobilization and inactivity. Immobilizing central nervous system conditions such as spinal cord injury, craniocerebral trauma and stroke are often associated with contractures. The term contracture applies to an abnormal state of fixed muscle shortening which limits joint mobility, but also to stiffening of a joint resulting from structural changes in the joint, also called "joint-contracture". Contractures usually result from disease of the nervous system, the muscles or joints. Central nervous system diseases are frequently accompanied by loss of upper motor neuron inhibition. As a result, the flexor muscles are often maintained in a position of contraction. Fibrous connective tissue replaces muscle fibers in the permanently contracted muscle, and a fibrous muscle contracture results. Fibrous muscle contractures can also be caused by ischemic injury to the muscle itself. Joint contractures are caused by structural damage to the joint, as occurs in degenerative joint disease, trauma or inflammation. Prolonged immobilization itself is also an important primary cause of joint contracture formation; it results in a sequence of events which lead to contraction of the joint capsule, atrophy of synovia and cartilage, encroachment of the joint by fibro-fatty tissue and heterotopic new bone formation, resulting in ankylosis. (Enneking W F, Horowitz M 1972; Akeson W H, Amiel D. Abel M F et al. 1986). The name "Charcot joint" is synonymous with all joint abnormalities related to neurologic deficits.

Contractures are frequently associated with immobility and severe dementia in the frail elderly in nursing homes. Alzheimer's disease is the leading cause of dementia, which is the major cause for institutionalization among the approximately 1.5 million persons in nursing homes in the United States.

It has been reported that patients with progressive dementia such as Alzheimer disease sometimes become immobile, but it had hitherto not been demonstrated that in progressive dementia, such as Alzheimer disease such dissolution of voluntary movement almost invariably leads to inactivity and immobility of many major joints in severely impaired patients with dementia. It had also not previously been demonstrated, that this loss of joint mobility almost always eventually results in the formation of joint contractures in patients with dementia.

Contractures have been speculated to be a stage of Alzheimer disease, and speculated to be useful as markers of disease severity in dementia (Volicer L. et al 1994), but prior to the work of the present inventors it has not been shown before that contractures correlate with severity of Alzheimer disease.

In the practice of medicine, the term contracture refers to an abnormal permanent shortening or shrinkage of the muscles, tendons, joint capsules and other tissues, associated with and necessary for the motion of a joint. The term contracture also refers to the resulting persistent flexion or distortion of the joint. In all cases, the term contracture implies loss of mobility of the joint. The term joint contracture is applied to the immobilization of a joint, usually, but not always in a position of flexion.

Currently employed measurements for staging severe dementia have limited value. Some of these presently used instruments, such as the Glasgow Coma Scale (Benesch C. G., McDaniel K. D., Cox C. et al 1993), have limited value, because they were not specifically developed for assessing severe dementia. The validity of other instruments, such as the BANS-S (Volicer L., Hurley A. C., Lahti D. C. et al 1994), has not been substantiated with respect to the use of contractures as a measure of dementia severity.

The System For Diagnosis And Staging of Dementia By Neurologic Examination (Franssen E. H., Reisberg B., U.S. Pat. No. 5,150,716, 1992) is extremely useful for gauging severe stage dementia. However, its use is limited once contracture formation has occurred.

Presence and prevalence of contractures has been used to assess the severity of traumatic brain injury (Wong P. P., Doman A. M., Keating A. M. et al 1994) but has not been used in a system to stage dementia severity or to assess the quality of care.

Joint immobilization, accompanied by contracture formation can result from diseases which immobilize because of their nature, such as diseases which cause paralysis or severe muscle wasting. Conversely, joint immobilization can cause muscle wasting, which can promote further contracture formation.

Joint immobilization, accompanied by contracture formation has also been speculated to be caused by disuse, resulting from a prolonged cessation of physical activities, such as occurs in conditions that are accompanied by severe loss of motivation and by lack of physical and mental stimuli in the environment (institutionalization syndrome), (Rader M. C., Vaughen J. L. 1994; Miller M. B. 1975).

Forced joint immobilization by use of physical restraints can have detrimental effects on joints (Conolly, J. 1856) and can cause joint contractures (McLardy-Smith P., Burge P. D., Watson N. A. 1986).

The immobile elderly and demented person is prone to contracture formation (Selikson S., Dainus K., Hamerman D. 1988). Improper positioning in these persons can cause nerve compression or muscle spasm resulting in additional contracture formation. Lack of physical activities alone (Kottke F. J. 1966; Gibbs J., Hughs S., Dunlop D. et al 1993) or immobility in these patients can also lead to disuse of joints and thus could also cause contracture formation.

BRIEF DESCRIPTION OF THE INVENTION

The invention relies upon the connection, discovered by the present inventors, of the strong correlation between contractures and the presence of advanced stage dementia.

The term "contracture" is here applied to a permanent loss of mobility of a large synovial joint, i.e., the shoulder joint, elbow joint, wrist joint, hip joint, knee joint and ankle joint, due to either permanent shortening of the muscles which move the joint or to structural changes of the joint and its supporting tissues that result in restriction of its mobility, or to a combination of these causes.

To practice the invention, a determination is made of the existence and the extent of the loss of mobility of a joint by measuring the range of motion of the joint in the plane(s) relevant to its normal function. Thus, flexion and extension of a joint are measured in the shoulder, elbow, wrist, hip, knee and ankle; abduction and adduction are measured in the shoulder, wrist and hip, rotation is measured in the shoulder, elbow (pronation and supination) and hip, and eversion and inversion are measured in the ankle joint. Conventionally, extension of the ankle joint is called "plantar flexion", and flexion of the ankle joint is called "dorsiflexion".

The range of motion of the joint is determined by moving the joint by an external force, i.e., by the examiner. This procedure is known by the term "passive range of motion determination". The passive range of motion is commonly expressed in degrees; one degree is the 360th part of the circumference of a circle.

The extent of loss of passive range of motion is expressed in the number of degrees of limitation, or as a percentage of the normal full passive range of motion.

The passive range of motion of a joint is measured by very slow and regular movement of the supported joint, up to a point where further passive movement is impossible because of either springy or completely unyielding resistance and because further passive movement causes considerable discomfort in the examinee. A severe contracture exists when the passive range of motion of a joint is 50% or less of its normal range of motion.

The passive range of motion can be measured by visual assessment or by various instrumental methodologies, such as radiography or goniometry.

We have discovered that the late stage of Alzheimer disease, by far the most common form of dementia, is invariably associated with a general immobility. We have also discovered, that loss of joint function with contracture formation is highly associated with late stage Alzheimer disease.

We have also discovered, that the formation of joint contractures can also occur at an earlier point in the course of Alzheimer disease.

We have also discovered that immobility in Alzheimer disease results in the formation of multiple joint contractures.

BRIEF DESCRIPTION OF THE DRAWINGS

FIG. 2 is a graph of the percentages and numbers of patients with contractures in community and nursing home residences in the five functional categories. The numbers in parenthesis at the bottom of the graph indicate the number of patients residing in the community and in the nursing home respectively, for each of the five functional categories. The numbers in parenthesis within the columns indicate the number of patients with contractures in each of the residential settings for the five functional categories.

DETAILED DESCRIPTION OF A PREFERRED EMBODIMENT

Figure 1:
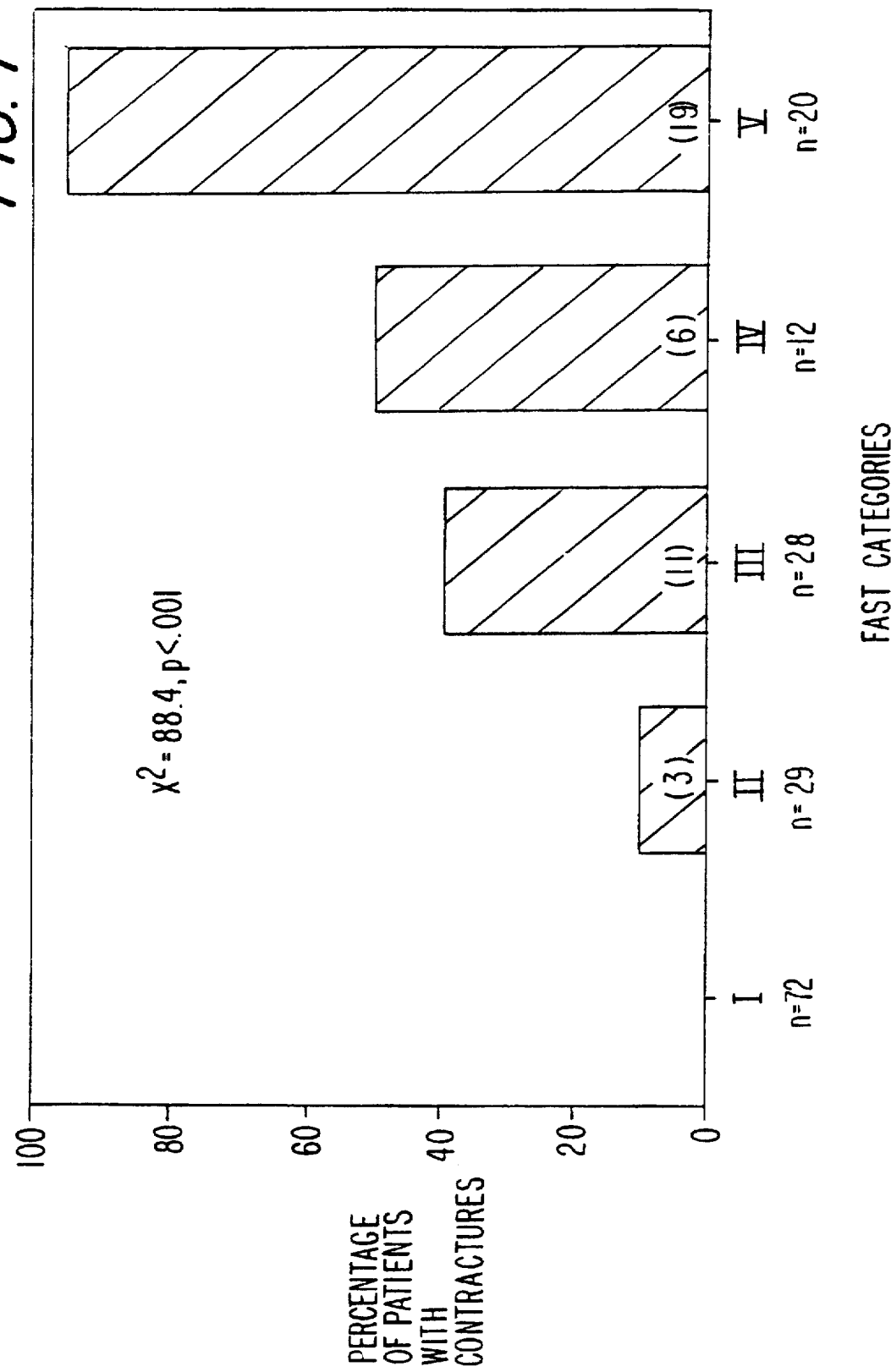
FIG. 1 is a graph of the percentage of patients with contractures in the five functional categories as follows: I, ADL deficient; II, Semi-incontinent; III, Semi-nonverbal, IV, Nonambulatory; and V, Immobile. The numbers in parenthesis indicate the number of patients with contractures in the 5 functional categories.

In accord with the present invention, measures were derived from existing examination methods common to the practice of rehabilitation medicine and widely used to assess joint mobility in patients with trauma or disease of the central nervous system, muscles or joints.

Specifically, these measures consisted of a determination of the passive range of motion, that is, moving the joint by an external source, in order to assess the functionality of the joint.

The joint was deemed rigidly non-functional, when a 50% limitation of its passive range of motion existed in one main direction of its normal function.

The criterion for such a limitation of passive range of motion was the inability to move the joint by applying a steady external force, beyond the point that is half the arc of its normal range of motion, because of either unyielding or springy resistance, whether or not associated with evidence of discomfort.

This range of motion determination was made for all large synovial joints of the two upper and the two lower extremities, e.g.; the shoulders, the elbows, the wrists, the metacarpo-phalangeal joints, the hips, the knees and the ankles.

The following range of motion determinations were made:

Shoulder:
    flexion with rotation of scapula
    extension with rotation of scapula
    abduction with rotation of scapula
    adduction with rotation of scapula Elbow:
    flexion
    extension Wrist:
    dorsal flexion
    volar flexion Hip:
    flexion (with bent knee)
    extension
    abduction
    adduction Knee:
    flexion
    extension Ankle:
    flexion; also called: dorsiflexion
    extension, also called: plantar flexion Contractures occurred in 3% of patients who were moderately severely cognitively impaired, as measured by the Mini Mental State Examination (MMSE), i.e., who had MMSE scores of greater than zero. In comparison, contractures occurred in 60% of patents who were severely cognitively impaired, i.e., who had MMSE scores of zero.

The inventors have unexpectedly discovered that the present invention can be employed to assess progression of loss of function in patients with Alzheimer disease, because no contractures were present in patients with deficient activities of daily life (ADL) alone; patients, who in addition to deficient ADL function also were semi-incontinent, had a contracture frequency of 10%; patients who in addition to deficient ADL functions and incontinence were also semi-nonverbal, had a contracture frequency of 39%; patients who in,addition to deficient ADL functions, incontinence and nonverbality were also nonambulatory, had a contracture frequency of 50%; and, patients who in addition to deficient ADL functions, incontinence, nonverbality and nonambulatory status were also immobile, had a contracture frequency of 95%. The differences in the prevalence of contractures among the five functional categories was highly significant (chi square=88.4, p<0.001).

The inventors unexpectedly discovered that the degree of functional decline as measured by the Functional Assessment Staging (FAST) scale strongly correlated with the occurrence of contractures (r=0.70, p<0.001).

The inventors also unexpectedly discovered, that contractures in moderately severe and severe stage Alzheimer disease occur in the large synovial joints, i.e., the shoulders, the elbows, the wrists, the hips, the knees and the ankles.

The contractures in moderately severe and severe stage Alzheimer disease occur in a position of flexion and/or adduction of the joint, with exception of the ankle joint where they also can occur in a position of extension (i.e., "plantar flexion").

Contractures in moderately severe and severe stage Alzheimer disease involve multiple joints: contractures (when present) occurred in one extremity in 2.5% of patients manifesting contractures, contractures occurred in 2 or more extremities in 97.5% of all patients manifesting contractures studied, and contractures occurred in all 4 extremities in 69% of all patients manifesting contractures studied.

Advantages of the Assessment Procedure

This invention has accomplished the following:

1) It provides a reliable, cognition independent, method for staging dementia.
2) It provides an objective, observationaly based, staging instrument capable of tracking the course of dementia when cognition-dependent measures bottom out and other cognition-independent measures cannot be applied to the fullest extent.
3) It provides an instrument for evaluating motor system impairment in demented patients.
4) It provides an objective method for the evaluation of the quality of care and quality of life where no such instrument presently exists.

Patients were selected who were baseline or follow-up participants in a longitudinal study of AD at the New York University Aging and Dementia Research Center and who were diagnosed at baseline with probable AD according to the criteria established by the National Institute of Neurological and Communicative Disorders and Stroke-Alzheimer's Disease and Related Disorders Association. Either the baseline evaluation or where applicable, the most recent follow-up evaluation, was used. Baseline examinations were conducted in the outpatient research setting. Follow-up examinations were conducted in the outpatient research setting, or, when necessary, in the patient's home residence or nursing home residence. The institutionalized patients of this study resided in 27 different nursing homes in the greater New York metropolitan area. At baseline, every patient received a physical, a neurological and a psychiatric examination, a routine examination of blood and urine, an electrocardiogram, a comprehensive neuropsychologic evaluation, and either a computed tomographic (CT) or a magnetic resonance imaging (MRI) brain scan. Follow-up evaluation always included at least physical and neurologic examinations as well as cognitive and functional assessment. Exclusion criteria at baseline were non-AD related causes of cognitive impairment (e.g., cerebrovascular accident, head trauma resulting in neurologic sequelae, alcoholism or drug abuse, history of previous psychiatric hospitalization, a Modified Ischemia Scale (Rosen W G et al. 1980) score of 4 or greater, and non-AD related causes of functional impairment (e.g., cancer, moderate to severe diabetes mellitus, cardiac—or pulmonary diseases, diseases of bones, joints, muscles or peripheral nerves). Evidence of the occurrence of an overt stroke after the baseline evaluation, as obtained either from the medical history or from the neurological examination, was an additional exclusion criterion applied at follow-up.

Measures

Magnitude of cognitive impairment was assessed using the Mini-Mental State Examination (MMSE) (Folstein M F et al 1975). The degree of functional impairment was assessed with the Functional Assessment Staging (FAST) (Reisberg B et al 1984) scale, an ordinal scale which specifically assesses progressive functional deterioration in AD. The FAST scale ranges from stage 1 signifying no functional deficit, to stage 7, at which point functional deficits are of sufficient magnitude for the patient to require continuous assistance and supervision. Patients at FAST stages 6 or greater, manifest deficits in one or more basic activity of daily life skills. FAST stages 6 and 7 are subdivided into 11 successive substages, enumerated with letters 6a to 6e, and 7a to 7f, based upon explicitly defined deficiencies (Table 1). The increasing FAST scores represent incremental functional deficiency; the assigned FAST score indicates the highest successive ordinal level of deficiency. In uncomplicated AD, progression of functional decline, as assessed by the FAST, generally proceeds in an hierarchical ordinal pattern. The validity of this sequence has been evaluated and confirmed by Guttman's method of scalogram analysis (Sclan S G, Reisberg B 1992). Strong relationships exist between the FAST stages and independent cognitive measurements of AD severity.

Procedures

All patients who participated in this study had deficiencies in the performance of basic activities of daily life (ADL) of sufficient severity to require at least some degree of physical assistance. Operationally, this was defined as a FAST stage of 6 or 7. The patient population was divided into five broad functional categories, based on the FAST stages and substages. Each functional category corresponds to a landmark in the course of functional decline. The functional categories studied were: I) ADL deficient; II) semi-incontinent; III) semi-nonverbal; IV) nonambulatory; and V) immobile. The deficits are incremental. The adjective "semi" indicates that the deficit in question is becoming apparent but may not be entirely manifest at all times, i.e., semi-incontinent signifies occasional or more frequent incontinence over the past few weeks, and semi-nonverbal implies some remaining use of words. Table I shows the five functional categories with corresponding FAST stages and substages.

Degree of passive range of motion was assessed in the upper extremities, i.e., the shoulders, elbows and wrists, and in the lower extremities, i.e., the hips, knees and ankles. Assessment consisted of very slow and gradual flexion, extension, abduction or adduction. This was conducted by the examiner up to the point where passive resistance, either springy or completely unyielding, made further motion impossible without significant discomfort to the patient.

The term "contracture" was used in a functional sense, and it indicated a permanent loss of joint mobility, measured through the determination of the passive range of motion of a joint. For this study, a contracture was defined as a limitation of 50% or greater of the passive range of motion of the joint, secondary to permanent muscle shortening, ankylosis or a combination of the two. Contractures were always associated with the involved joint in a position of flexion, with the exception of the ankle joint, where contractures also occurred in the extended joint (i.e., the joint in "plantar flexion").

Results

The patients in this study represented a consecutive sample of all patients with AD in FAST stages 6 and 7, seen in a time period of 6 years. All patients were seen by the same evaluator(s). A total of 161 patients were studied (113 women and 48 men). The mean age was 75.3 years (±8.6 years); ages ranged from 50 to 95 years. Of the 161 evaluations, 84 (54 women and 30 men) were conducted in the outpatient research setting, 18 (13 women and 5 men) in the residential home setting, and 59 (46 women and 13 men) in the nursing home where the patient resided at the time of the evaluation. Table 2 shows the age distribution and MMSE scores of the patients in the five functional categories. As can be seen in Table 2, there exists a close relationship between the degree of cognitive decline and the magnitude of functional impairment.

Out of the total study population, 76% of the patients (n=122) had no contractures, while 24% of the patients (n=39) had a contracture involving at least one large joint of at least one extremity. Degree of functional decline as measured by the FAST strongly correlated with the occurrence of contractures (r=0.70, p<0.001). FIG. 1 shows the percentages of patients with contractures in each of the five functional categories. The prevalence of contractures was significantly different among the five functional categories ($\chi^2$=88.4, p<0.001).

Multiple regression analysis with contractures as dependent variable and FAST and age as independent variables were carried out for the total patient population, and for women and men separately. For the entire patient sample (n=161), FAST accounted for 49% of the variance ($R^2$=0.49, F=153. 1, p<0.001); age did not add significant additional variance. For the women (n=113) FAST accounted for 47% of the variance observed ($R^2$=0.47, F=98.6, p=<0.001); age did not add additional variance. For the men (n=48), FAST accounted for 55% of the variance observed ($R^2$=0.55, F=56.7, p<0.001), while age added an additional 4% to the variance observed ($R^2$=0.59, F=32.5, p<0.05). Men with contractures had a lower mean age (68.5 years±6.8 years) than men without contractures (76.0 years±7.8 years). Of the 102 patients, residing in the community settings 7 (7%) had contractures. Of the 59 institutionalized patients, 32 (54%) had contractures. The mean FAST substage for the community residing patients was 6c; the mean FAST substage for the nursing home residing patients was 7b.

All but two of the 39 patients with contractures had an MMSE score of zero. In all but one of the patients who had contractures, at least 2 extremities were involved, and in more than two-thirds of patients who had contractures (69%), these were present in all four extremities (Table 3). Thirty of the 39 patients with contractures (77%) had involvement of at least one upper and at least one lower extremity; seven patients (18%) had contractures of one or both upper extremities without contractures in the lower extremities (including one patient who had bilateral amputation of the lower extremities above the knee). Two patients (5%) had contractures of one or both lower extremities alone. Thirteen (33%) of the patients with contractures had observed presence or a documented history of decubital ulceration. With respect to residential setting, 7 of the 39 patients with contractures (18%) lived in the community and the remaining 32 patients (82%) resided in a nursing home. The relationship between contracture prevalence, functional impairment and residential setting is shown in FIG. 2.

Discussion

Nearly a quarter of all patients studied had contractures. More than three quarters of the patients who had lost the ability to walk had contractures, and these deformities occurred in all but one of the 20 severe stage AD patients who were immobile.

The observation that men with contractures were significantly younger than men without contractures was somewhat surprising. This phenomenon was not observed in women. One possible explanation is that older men with contractures die more rapidly and were therefore underrepresented in this study, but further investigation is needed to clarify this finding.

Several observations strongly suggest that contractures are a fundamental outcome of AD and not an independent concurrent condition. First, the increase in contracture frequency closely paralleled disease severity. The correlation noted between contracture occurrence and the functional stage of AD (FAST stage), was 0.70. The FAST stages in turn, have previously shown strong correlations with measures of progressive cognitive change in AD. It is unlikely, that an independent intercurrent condition as cause of contracture formation would so closely follow the progression of AD. Secondly, contractures occurred nearly universally in all AD patients with severe dementia who were immobile as a result of the disease. Thirdly, in the majority of patients with contractures, all extremities were involved, which makes it less likely that a peripheral, locally operating factor, is the cause of contracture formation. Neurologic signs, such as extensor plantar reflexes (Babinski sign), hand- and foot grasp reflexes, dyskinesia, myoclonus, and paratonic muscle rigidity, are common in severe stage AD. These neurologic signs are indicative of a general motor system dysfunction in AD, which may also be relevant for the occurrence of contractures. We observed that limitation of joint mobility was almost always associated with the joint in a position of flexion and with adduction of the shoulder and hip. This supports the view that paraplegia in flexion of cerebral origin as described by Yakovlev, with relative hyperactivity of the flexors, permanent flexion contractures of the extremities and with paratonia (that is, with external stimulus dependent rigidity), is a clinical characteristic of end stage AD. Contractures are also part of acute neurologic conditions, associated with immobility and abnormal muscle tone. For instance, an 84% incidence of contractures in the large joints of the extremities has been reported in patients with severe head injury, most of whom had been comatose for more than two weeks. Nonambulatory status and immobility, in combination with flexor hypertonicity, probably constitute the most important risk factors for contracture formation in AD. However, in the individual patient with AD, the actual formation of a contracture may have a complex etiology, and intercurrent conditions may constitute additional risk factors. In our study, 7 of 39 patients with contractures (18%) had a history of hip fracture. Osteoarthritis, a common condition in older persons, is another potential risk factor. Stroke may also be associated with contracture formation, however patients with this condition were excluded.

Contractures can interfere with nursing care, functional activities and cosmesis. Contractures can cause considerable discomfort (Yarkony G M et al. 1985). Contracture formation is believed to be an at least in part, preventable condition in control in central nervous system disorders associated with decreased mobility (Yarkony G M et al. 1985, Frank (et al. 1984, 1987) by provision of special care. Hence, occurrence and extent of contracture formation can be a measurement for assessing quality of care in patients with dementia. Contractures are known to be associated with other forms of disability and distress, hence presence and extent of contracture formation can be a measurement for assessing quality of life in patients with dementia.

TABLE 1

Functional Categories, FAST* Stages and Substages

| FUNCTIONAL CATEGORY | FAST STAGE | FAST SUBSTAGE | CHARACTERISTICS |
|---|---|---|---|
| I ADL deficient | 6 | a | Improperly putting on clothes without assistance or cuing (e.g., may put street clothes on over night clothes, or put shoes on wrong feet, or have difficulty buttoning clothing) occasionally or more frequently over the past weeks.** |
| | | b | Unable to bathe properly (e.g., difficulty adjusting bath-water temperature) occasionally or more frequently over the past weeks.** |
| | | c | Inability to handle mechanics of toileting (e.g., forgets to flush the toilet, does not wipe properly, or improperly disposes of toilet tissue) occasionally or more frequently over the past weeks.** |
| II Semi-incontinent | 6 | d | Urinary incontinence (occasionally or more frequently over the past weeks).** |
| | | e | Fecal incontinence (occasionally or more frequently over the past weeks).** |
| III Semi-nonverbal | 7 | a | Ability to speak limited to approximately a half a dozen intelligible different words or fewer, in the course of an average day or in the course of an intensive interview.*** |
| | | b | Speech ability limited to the use of a single intelligible word in an average day or in the course of an intensive interview (the person may repeat the single intelligible word over and over).*** |
| IV Nonambulatory | 7 | c | Ambulatory ability lost (cannot walk without personal assistance).*** |
| V Immobile | 7 | d | Cannot sit up without assistance (e.g., the individual will fall over if there are no lateral rests [arms] on the chair).*** |
| | | e | Loss of ability to smile.*** |
| | | f | Loss of ability to hold up head independently.*** |

*Functional Assessment Staging. Adapted with permission from Reisberg B. Geriatrics 1986; 41:30–46. The FAST stage is the highest ordinally enumerated score. Interviewers are instructed to check the highest consecutive level of disability.
**Scored primarily on the basis of information obtained from knowledgeable informants.
***Scored primarily on the basis of direct observation of the patient.

TABLE 2

Patient Characteristics

| Functional Category | | N | Age* | MMSE** Score* |
|---|---|---|---|---|
| I | ADL deficient | 72 | 74.5 ± 8.4 | 11.0 ± 6.2 |
| II | Semi-incontinent | 29 | 76.5 ± 8.9 | 5.3 ± 4.6 |
| III | Semi-nonverbal | 28 | 75.5 ± 8.7 | 0.1 ± 0.2 |
| IV | Nonambulatory | 12 | 73.9 ± 8.7 | 0.0 ± 0.0 |
| V | Immobile | 20 | 77.1 ± 9.2 | 0.0 ± 0.0 |
| | Total patients | 161 | 75.3 ± 8.6 | 5.9 ± 6.7 |

*Values are mean ± S.D.
**MMSE, Mini Mental State Examination.

TABLE 3

Numbers and Percentages of Subjects with Contractures Involving Respectively One, Two, Three and Four Extremities in each of the Functional Categories.

| | | | EXTREMITIES | | | |
|---|---|---|---|---|---|---|
| Functional Category | | N | One (%)* | Two (%)* | Three (%)* | Four (%)* |
| I | ADL deficient | — | — | — | — | — |
| II | Semi-incontinent | 3 | 0 (0) | 2 (67) | 0 (0) | 1 (33) |
| III | Semi-nonverbal | 11 | 0 (0) | 1 (9) | 0 (0) | 10 (91) |
| IV | Nonambulatory | 6 | 0 (0) | 2 (33) | 1 (17) | 3 (50) |
| V | Immobile | 19 | 1 (5) | 3 (16)** | 2 (11) | 13 (68) |
| | Total patients | 39 | 1 (3) | 8 (21) | 3 (8) | 27 (69) |

*Percentage of patients with contractures involving this number of extremities in the Functional Categories.
**One patent with bilateral above the knee amputation.

What is claimed is:

1. A method for determination of the progression of diagnosed Alzheimer's disease in an elderly patient comprising determining the presence of a contracture by measuring the passive range of motion of a joint, wherein a positive indication of the presence of the disease is a limitation of 50% or greater of the passive range of motion of the joint, secondary to permanent muscle shortening or ankylosis.

2. The process for developing a cognition independent test for the staging of advanced dementia by utilizing the demonstration of the presence of contractures as a measure of dementia severity, comprising:

a) determining the passive range of motion of a joint as a measure for determining the presence of a contracture.

b) developing the methodology of the determination of the passive range of motion of a joint as a cognition-independent measure for staging the degree of functional loss in dementia whereby the determination of the presence of a contracture is established when a joint has lost 50% of its normal range of motion.

3. The process for developing a cognition independent test for the staging of advanced dementia by utilizing the demonstration of the presence of contractures as a measure of dementia severity, comprising:

a) determining the passive range of motion of a joint as a measure for determining the presence of a contracture.

b) developing the methodology of the determination of the passive range of motion of a joint as a cognition-independent measure for staging the degree of functional loss in dementia wherein the following are measured:

maximum range of motion in both shoulder joints,
measurements of maximum range of motion in both elbow joints,
the measurements of maximum range of motion in both elbow joints with measurements of maximum range of motion in both wrists joints,
the measurement of maximum range of motion in both wrists joints with measurement of maximum range of motion in both hip joints,
the measurements of maximum range of motion in both hip joints with measurement of maximum range of motion in both knee joints,
and the measurements of maximum range of motion in both knee joints with measurement of maximum range of motion in both ankle joints,
and said measurements are weighted using an algorithmic mathematical procedure.

4. The method of claim 2 wherein the measurements are measurements of joint contracture, and used in staging dementia severity or loss of functional capability.

5. The method of claim 3 wherein the measurements are measurements of joint contracture, and used in assessing quality of care.

6. The method of claim 3 wherein the measurements are measurements of joint contracture, and used in assessing quality of life.

\* \* \* \* \*